(12) United States Patent
Jakobsen et al.

(10) Patent No.: US 10,603,442 B2
(45) Date of Patent: Mar. 31, 2020

(54) ACCESSORY DEVICE WITH SNAP FEATURE

(71) Applicant: Novo Nordisk A/S, Bagsvaerd (DK)

(72) Inventors: Nikolaj Eusebius Jakobsen, Soeborg (DK); Ian McLoughlin, Copenhagen OE (DK)

(73) Assignee: Novo Nordisk A/S, Bagsvaerd (DK)

( * ) Notice: Subject to any disclaimer, the term of this patent is extended or adjusted under 35 U.S.C. 154(b) by 204 days.

(21) Appl. No.: 15/505,423

(22) PCT Filed: Aug. 25, 2015

(86) PCT No.: PCT/EP2015/069396
§ 371 (c)(1),
(2) Date: Feb. 21, 2017

(87) PCT Pub. No.: WO2016/030348
PCT Pub. Date: Mar. 3, 2016

(65) Prior Publication Data
US 2017/0266389 A1    Sep. 21, 2017

(30) Foreign Application Priority Data

Aug. 25, 2014   (EP) .................................... 14182145
Nov. 3, 2014    (EP) .................................... 14191476

(51) Int. Cl.
*A61M 5/315*    (2006.01)
*A61M 5/20*     (2006.01)
(Continued)

(52) U.S. Cl.
CPC .......... *A61M 5/31568* (2013.01); *A61M 5/20* (2013.01); *A61M 5/24* (2013.01);
(Continued)

(58) Field of Classification Search
CPC .......... A61M 5/31525; A61M 5/31533; A61M 5/31545; A61M 5/31546; A61M 5/31548;
(Continued)

(56) References Cited

U.S. PATENT DOCUMENTS 4,863,199 A    9/1989  Hojo et al.
4,932,941 A    6/1990  Min et al.
(Continued)

FOREIGN PATENT DOCUMENTS

DE    20110690 U1    9/2001
JP    3181663 B2     7/2001
(Continued)

*Primary Examiner* — Kami A Bosworth
(74) *Attorney, Agent, or Firm* — Wesley Nicolas

(57) ABSTRACT

A logging device adapted to be attached to a pen drug delivery device (210) and capture a property value related to the dose amount of drug expelled from the drug delivery device during an expelling event, the logging device comprising a bore in which a snap lock with a flexible wire portion is arranged circumferentially in the bore, the wire being adapted to be moved laterally by a projection on the pen device and subsequently snap inwardly when the pen device is inserted axially in the bore. In this way an axial snap lock is provided between the logging device and the drug delivery device.

12 Claims, 6 Drawing Sheets

(51) Int. Cl.
*A61M 5/24* (2006.01)
*G06F 19/00* (2018.01)

(52) U.S. Cl.
CPC ..... *G06F 19/3468* (2013.01); *A61M 2205/33* (2013.01); *A61M 2205/6036* (2013.01); *A61M 2205/6045* (2013.01)

(58) Field of Classification Search
CPC ............ A61M 5/3155; A61M 5/31551; A61M 5/31553; A61M 5/31556; A61M 5/3156; A61M 5/31568; A61M 2005/2006; A61M 2005/3125; A61M 2005/3126; A61M 2205/3317; A61M 2205/6045; A61M 2205/6054

See application file for complete search history.

(56) References Cited

U.S. PATENT DOCUMENTS

| | | | |
|---|---|---|---|
| 6,482,185 | B1 | 11/2002 | Hartmann |
| 8,968,257 | B2 | 3/2015 | Dasbach et al. |
| 2009/0318865 | A1 | 12/2009 | Moller et al. |
| 2011/0009812 | A1* | 1/2011 | Brown .................. A61B 5/155 604/31 |
| 2012/0053527 | A1* | 3/2012 | Cirillo ............... A61M 5/31525 604/189 |
| 2012/0072236 | A1* | 3/2012 | Atkin .................. A61M 5/3155 705/3 |
| 2014/0088494 | A1 | 3/2014 | Shearer, Jr. et al. |
| 2014/0194829 | A1* | 7/2014 | Baek ................. A61M 5/31551 604/207 |
| 2015/0025470 | A1* | 1/2015 | Baran .................. A61M 5/178 604/187 |
| 2015/0343152 | A1* | 12/2015 | Butler ............... A61M 5/31551 604/207 |

FOREIGN PATENT DOCUMENTS

| | | |
|---|---|---|
| JP | 2012519028 A | 8/2012 |
| JP | 2013534831 A | 9/2013 |
| WO | 2003005891 A1 | 1/2003 |
| WO | 04065224 A2 | 8/2004 |
| WO | 05031174 A2 | 4/2005 |
| WO | 2006004552 A1 | 1/2006 |
| WO | 2007107564 A1 | 9/2007 |
| WO | 2010037828 A1 | 4/2010 |
| WO | 2010052275 A2 | 5/2010 |
| WO | 2010098931 A1 | 9/2010 |
| WO | 2011032883 A1 | 3/2011 |
| WO | WO-2013050535 A2 * 4/2013 .......... A61M 5/1452 |
| WO | 2013113818 A1 | 8/2013 |
| WO | 2013120773 A1 | 8/2013 |
| WO | 2013120775 A1 | 8/2013 |
| WO | 2013120776 A1 | 8/2013 |
| WO | 2014173434 A1 | 10/2014 |
| WO | WO2014/173434 * 10/2014 .............. A61M 5/24 |

* cited by examiner

ACCESSORY DEVICE WITH SNAP FEATURE

CROSS-REFERENCE TO RELATED APPLICATIONS

This application is a 35 U.S.C. § 371 National Stage application of International Application PCT/EP2015/069396 (published as WO 2016/030348), filed Aug. 25, 2015, which claims priority to European Patent Application 14182145.4, filed Aug. 25, 2014, and priority to European Patent Application 14191476.2, filed Nov. 3, 2014; the contents of which are incorporated herein by reference.

The present invention generally relates to medical devices for which the generation, collecting and storing of data are relevant. In specific embodiments the invention relates to devices and systems for capturing and organizing drug delivery dose data in an efficient and user-friendly way.

BACKGROUND OF THE INVENTION

In the disclosure of the present invention reference is mostly made to drug delivery devices comprising a threaded piston rod driven by a rotating drive member, such devices being used e.g. in the treatment of diabetes by delivery of insulin, however, this is only an exemplary use of the present invention.

Drug Injection devices have greatly improved the lives of patients who must self-administer drugs and biological agents. Drug Injection devices may take many forms, including simple disposable devices that are little more than an ampoule with an injection means or they may be durable devices adapted to be used with pre-filled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, from the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of ejection information from medication delivery systems.

Though some injection devices integrate this monitoring/acquisition mechanism into the device itself, e.g. as disclosed in US 2009/0318865 and WO 2010/052275, most devices of today are without it. The most widely used devices are purely mechanical devices either durable or prefilled. The latter devices are to be discarded after being emptied and so inexpensive that it is not cost-effective to build-in electronic data acquisition functionality in the device it-self. Addressing this problem a number of solutions have been proposed which would help a user to generate, collect and distribute data indicative of the use of a given medical device.

For example, WO 2007/107564 describes an electronic "add-on" module adapted to be attached to and measure signals generated by a mechanical pen device. The detected signals may be used to detect different events, e.g. different sounds indicating setting a dose respectively ejecting a dose. A memory stores detected doses together with a time stamp, e.g. for several months. The module is provided with wireless means for transmitting detected data to an external unit, e.g. computer or another portable device (e.g. cell phone, PDA) for further processing and visualization.

WO 2010/037828 discloses an arrangement for mounting such a module on a pen-formed drug delivery device, the module comprising a pair of flexible legs allowing it to be clamped onto the drug delivery device. Further external devices for a pen device are shown in U.S. Pat. No. 6,482,185 and WO 03/005891.

Having regard to the above, it is an object of the present invention to provide devices and methods allowing secure, easy and cost-effective operation of a drug delivery assembly comprising a user-mountable module.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first general aspect of the invention a logging device adapted to be releasably attached to a drug delivery device is provided, the drug delivery device comprising a drug reservoir or means for receiving a drug reservoir, drug expelling means comprising dose setting means allowing a user to set a dose amount of drug to be expelled, and a generally cylindrical coupling portion having a least one lateral projection, the logging device comprising electronic circuitry adapted to create a log of expelled dose amounts of drug. The electronic circuitry comprises sensor means adapted to capture, when the logging device is attached to a drug delivery device, a property value related to the dose amount of drug expelled from a reservoir by the expelling means during an expelling event. The logging device further comprises a generally cylindrical bore adapted to receive the coupling portion. The logging device comprises at least one individual snap lock adapted to engage a lateral projection on a drug delivery device, the individual snap lock comprising a flexible wire portion arranged circumferentially in the bore and being adapted to be moved laterally by the lateral projection and subsequently snap inwardly when the coupling portion is inserted axially in the bore, whereby an axial snap lock is provided between the logging device and the drug delivery device.

By this arrangement, using one or more separate wires, the snap-on force can be optimized to achieve both secure attachment and ease of use just as the wire material can be chosen so as to retain its strength over the lifetime of the add-on device thereby providing a robust fixation.

At least one individual snap lock may further comprise a pair of circumferentially arranged support structures serving as fulcrum points for the wire portion when the wire portion is moved laterally by the drug delivery device lateral projection when the coupling portion is inserted axially in the bore. By allowing the position of the fulcrum points to be determined during development varying degrees of pull-off/ put-on forces can be obtained. In contrast to wire material which normally is offered with standard diameters, the provision of pairs of fulcrum points allows the snap lock characteristics to be finely adjusted during the development by varying the distance between the points for a given wire diameter. The wire material will typical be a metal composition.

The logging device may be provided with a generally ring-formed wire locking member forming the wire portions of at least two individual snap locks. The ring-formed wire may be in the form of either a closed or an open ring.

The ring-formed wire locking member and the bore may be configured such that the ring-formed locking member can be inserted in the bore and snap non-releasable in place, i.e. the locking member cannot be removed without using a tool and/or without damaging the structures. In this way the elastic properties of the wire is utilized during both manufacture and subsequent use. Alternatively, a ring-formed member may be mounted in the cylindrical bore and adapted to hold the ring-formed locking member non-releasable in place.

In exemplary embodiments the sensor means is adapted to capture a property value in the form of an amount of rotation of a magnetic member arranged in the drug delivery device, the amount of rotation of the magnetic member corresponding to the amount of drug expelled from a reservoir by the expelling means.

A logging device as described above may be provided in combination with a drug delivery device comprising a drug reservoir or means for receiving a drug reservoir, drug expelling means comprising dose setting means allowing a user to set a dose amount of drug to be expelled, and a generally cylindrical coupling portion having a least one lateral projection, the logging device and the drug delivery device forming an assembly. The logging device is releasably attachable to the drug delivery device.

In a further aspect of the invention a medical system is provided comprising a logging device as described above, in combination with first and second drug delivery devices each comprising a drug reservoir or means for receiving a drug reservoir, drug expelling means comprising dose setting means allowing a user to set a dose amount of drug to be expelled, and a generally cylindrical coupling portion having a least one lateral projection. In the system each cylindrical coupling portion comprises coding means, and the logging device comprises coding means associated with the cylindrical bore. The coding means on the drug delivery devices respectively the logging device are configured to (i) allow the first drug delivery device to be received and releasably locked in the logging device bore, and (ii) prevent the second drug delivery device to be received and locked in the logging device bore. Indeed, this feature would be the case for any two completely different devices, thus the drug delivery devices in the system of the present invention are based on the same technology platform (see below).

In a yet further aspect of the invention a medical system is provided comprising first and second logging devices as described above, in combination with first and second drug delivery devices each comprising a drug reservoir or means for receiving a drug reservoir, drug expelling means comprising dose setting means allowing a user to set a dose amount of drug to be expelled, and a generally cylindrical coupling portion having a least one lateral projection. In the system each cylindrical coupling portion comprises coding means, and each logging device comprises coding means associated with the cylindrical bore. The coding means on the drug delivery devices respectively the logging devices are configured to (i) allow the first drug delivery device to be received and releasably locked in the first logging device bore, and prevent the second drug delivery device to be received and locked, and (ii) allow the second drug delivery device to be received and releasably locked in the second logging device bore, and prevent the first drug delivery device to be received and locked. The drug delivery devices in the system are based on the same technology platform.

"Technology platform" is meant to mean the basic structure upon which the injection devices in the system are based, e.g. the mechanism for setting and expelling a dose of fluid drug from a drug-filled cartridge. In order to be based on the same technology platform, the injection devices of the system must work by the same mechanical principles i.e. the individual constructional components of each injection device must be the same and interact in the same way. Technology platform products share underlying structures or basic architectures that are common across a group of products or that will be the basis of a series of products commercialized over a number of years. Several products may be derived from a common technology platform. Members of a product family normally have many common parts and assemblies. Thus, two drug delivery devices sharing the same technology platform may in accordance with the present invention have e.g. at least 50%, 75% or 90% interchangeable parts (excluding non-structural parts as e.g. labels). To be interchangeable the parts may be morphologically identical or they may be fully identical.

By providing a system with a coding it can be ensured to a high degree that a given logging device can be mounted only on the type of drug delivery device to which it is adapted to work, e.g. comprising a given drug in a given concentration.

In the above-described systems each logging device may comprise a ring-formed code member comprising the coding means and being mounted in the cylindrical bore. Each code ring may be adapted to hold the ring-formed locking member non-releasable in place. The corresponding code means may be of the key-and-slot type.

In a further more general aspect of the invention an assembly comprising a first unit and a second unit is provided, the first unit comprising a first generally cylindrical coupling portion having a least one lateral projection, and the second unit comprising a second coupling portion having a generally cylindrical bore adapted to receive the first coupling portion. The first unit comprises at least one individual snap lock adapted to engage a lateral projection on the second unit, the individual snap lock comprising a flexible wire portion arranged circumferentially in the bore and being adapted to be moved laterally by the lateral projection and subsequently snap inwardly when the coupling portion is inserted axially in the bore, whereby an axial snap lock is provided between the first and second units. The units may be provided with additional features as described above.

In a second general aspect of the invention an assembly is provided comprising a main unit, first and second flexible snap members, and first and second secondary units. Each secondary unit comprises a generally cylindrical coupling portion having coupling means, and coding means. The main unit comprises a generally cylindrical bore with a snap member in non-releasable engagement, the bore being adapted to receive a secondary unit coupling portion. Each snap member is provided with coupling means adapted to releasably engage the secondary unit coupling means, and coding means. The coding means on the secondary units respectively the snap members are configured to (i) allow the first secondary unit to be received and releasably locked in the main unit bore when the first snap member is mounted, and prevent the second secondary unit to be received and locked, and (ii) allow the second secondary unit to be received and releasably locked in the main unit bore when the second snap member is mounted, and prevent the first secondary unit to be received and locked.

By providing a snap member with integrated coding a given main unit can be provided with a coding feature in a cost-effective way.

The secondary unit coupling means may be provided with at least one lateral projection, the snap members being adapted to be moved laterally by a lateral projection and subsequently snap inwardly when a secondary unit is received and releasably locked in the main unit bore.

The snap members may be generally ring-formed, this allowing the ring-formed snap members and the bore to be configured such that the ring-formed snap member can be inserted in the bore and snap non-releasable in place. In this way a given assembled main unit can be used for all versions of a secondary unit, this allowing coding to take place after (almost) final assembly in a cost-effective way.

The corresponding coding means may comprise corresponding mechanical key structures allowing or preventing mating.

In an exemplary embodiment each secondary unit is in the form of a drug delivery device comprising a drug reservoir or means for receiving a drug reservoir as well as drug expelling means, and the main unit is a logging module comprising electronic circuitry adapted to create a log of expelled dose amounts of drug, the logging unit comprising sensor means adapted to capture a property value related to a dose amount of drug expelled from a reservoir by the expelling means during an expelling event, and processor means adapted to determine dose amounts based on captured property values.

The sensor means may be adapted to capture a property value in the form of an amount of rotation of a magnetic member arranged in a drug delivery device, the amount of rotation of the magnetic member corresponding to the amount of drug expelled from a reservoir by the expelling means.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of exemplary embodiments reference will be made to the use of insulin.

BRIEF DESCRIPTION OF THE DRAWINGS

In the following embodiments of the invention will be described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessarily can be assembled to provide a unitary or functional assembly during a given assembly procedure but is merely used to describe components grouped together as being functionally more closely related.

Figure 1A:
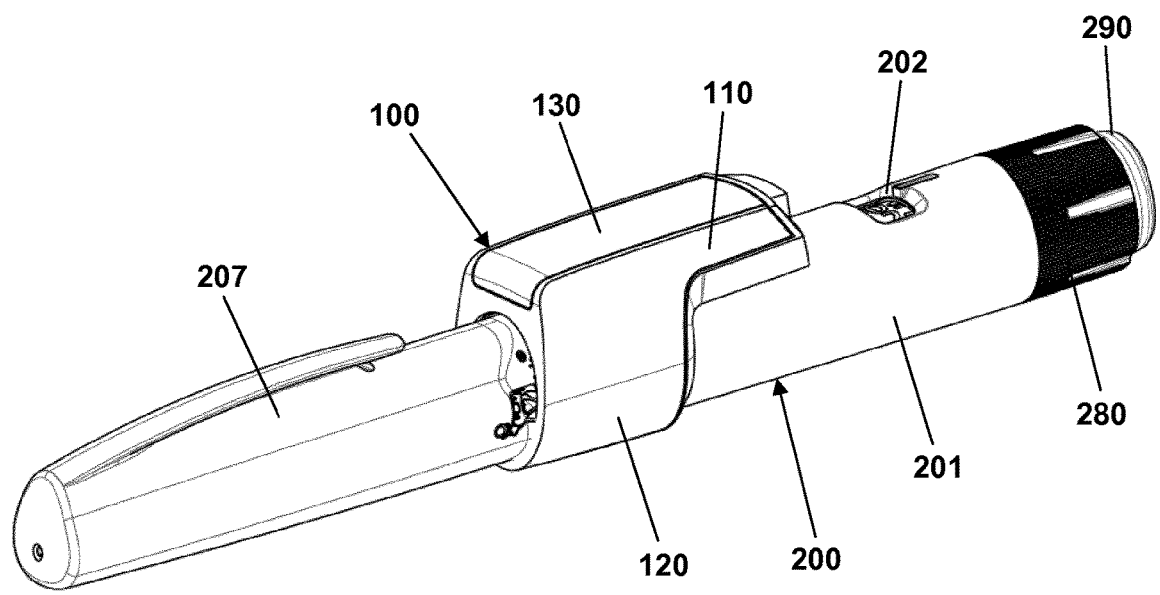
FIGS. 1A and 1B show a pen-formed drug delivery device with an electronic logging module.
Figure 1B:
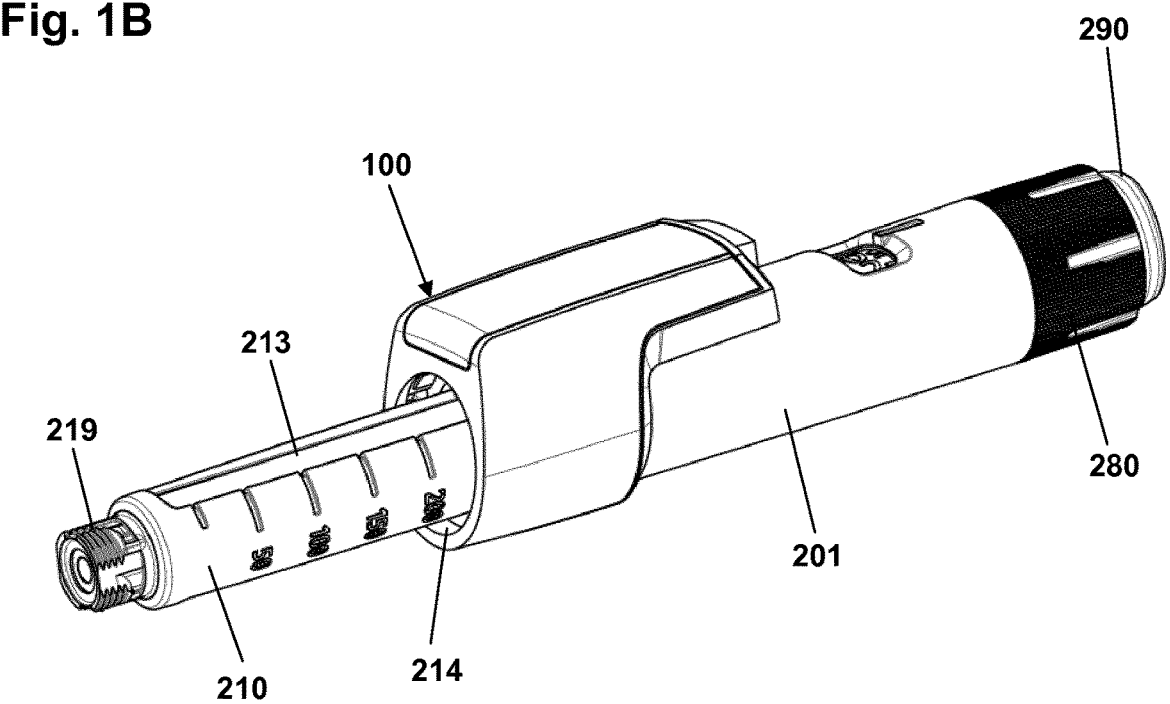

FIGS. 1A and 1B show a pen-formed drug delivery device 200 on which an electronic logging device (in the following termed logging module) 100 is mounted. In the present context the device represents a "generic" drug delivery device providing a specific example of a device in combination with which embodiments of the present invention is intended to be used or which can form a basis for aspects of the present invention.

More specifically, the logging module 100 comprises a body portion 110 and a ring-formed portion 120 allowing the module to be mounted on a generally cylindrical pen device. The body portion comprises electronic circuitry and sensor means allowing a property to be detected representing an amount of drug being expelled from the cartridge, as well as a display 130 for displaying data to a user. The ring portion comprises coupling means allowing the module to be securely and correctly mounted on the pen body. The electronic circuitry and the sensor means may in part be arranged in the ring portion.

The pen device 200 comprises a cap part 207 and a main part having a proximal body or drive assembly portion with a housing 201 in which a drug expelling mechanism is arranged or integrated, and a distal cartridge holder portion in which a drug-filled transparent cartridge 213 with a distal needle-penetrable septum is arranged and retained in place by a non-removable cartridge holder attached to the proximal portion, the cartridge holder having openings allowing a portion of the cartridge to be inspected as well as distal coupling means 219 allowing a needle assembly to be releasably mounted. The cartridge is provided with a piston driven by a piston rod forming part of the expelling mechanism and may for example contain an insulin, GLP-1 or growth hormone formulation. A proximal-most rotatable dose member 280 serves to manually set (or dial) a desired dose of drug shown in display window 202 and which can then be expelled when the button 290 is actuated. Depending on the type of expelling mechanism embodied in the drug delivery device, the expelling mechanism may comprise a spring as in the shown embodiment which is strained during dose setting and then released to drive the piston rod when the release button is actuated. Alternatively the expelling mechanism may be fully manual in which case the dose member and the actuation button moves proximally during dose setting corresponding to the set dose size, and then is moved distally by the user to expel the set dose.

FIGS. 1A and 1B show a drug delivery device of the pre-filled type, i.e. it is supplied with a pre-mounted cartridge and is to be discarded when the cartridge has been emptied. In alternative embodiments the drug delivery device may be designed to allow a loaded cartridge to be replaced, e.g. in the form of a "rear-loaded" drug delivery device in which the cartridge holder is adapted to be removed from the device main portion, or alternatively in the form of a "front-loaded" device in which a cartridge is inserted through a distal opening in the cartridge holder which is non-removable attached to the main part of the device.

Figure 2:
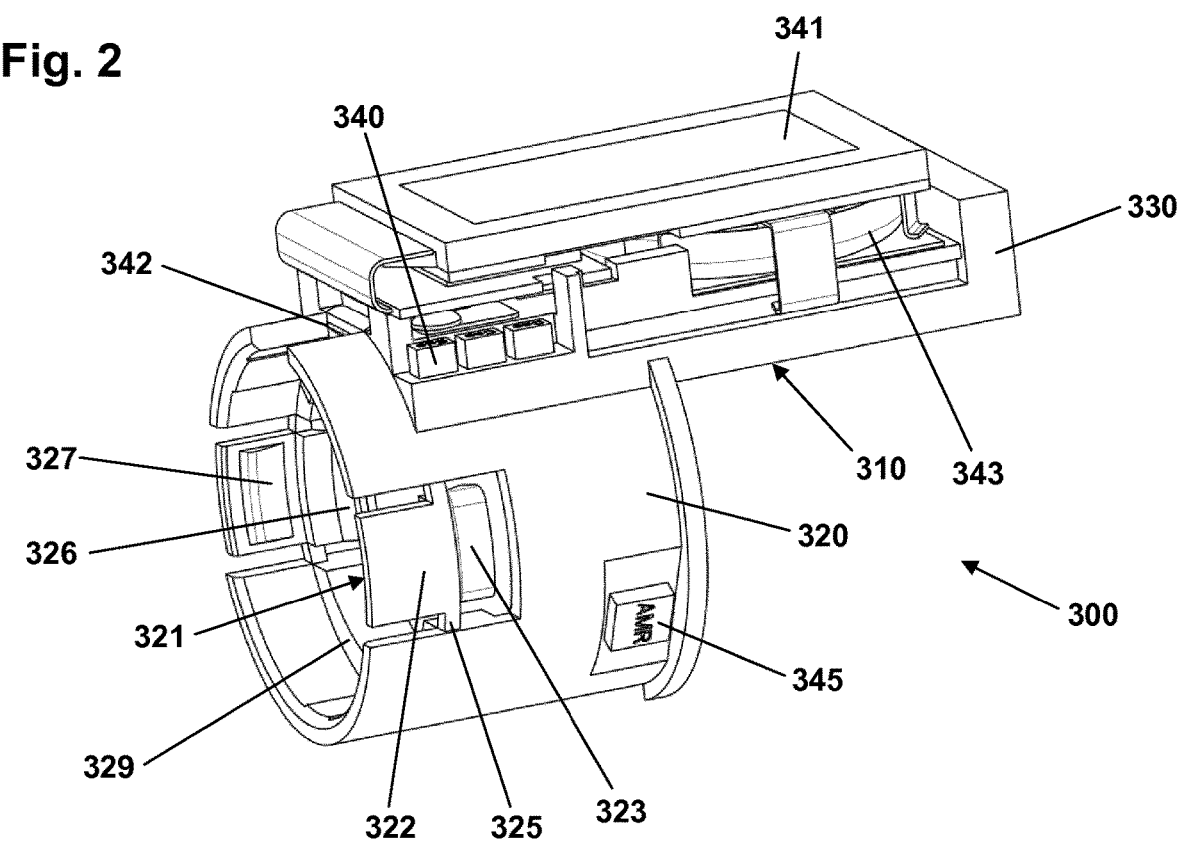
FIG. 2 shows the interior of a logging module.

Turning to FIG. 2 a first exemplary embodiment of a logging module 300 is shown in which the exterior cover portion has been removed to reveal the interior design and components, the cover portion providing the exterior oriented towards the user whereas the exterior surface facing the pen when the module is in its mounted position is made up by the main body, see below.

The module comprises a main body 310 having a generally cylindrical ring-formed portion 320 and a body portion 330 on which the majority of the electronic circuitry is mounted. The main body is formed from a LDS polymer whereby integrated wiring can be achieved by using LDS (Laser Direct Structuring) technology, the polymer having elastic properties allowing a flexible hinged latch to be formed integrally. More specifically, the ring portion comprises an inner generally cylindrical surface adapted to be mounted on a drug delivery pen body as well as a pair of opposed integrally formed coupling structures 321 adapted to engage corresponding coupling structures on the pen device to assure that the module is securely mounted. The distal part of the ring portion has a larger diameter with a distally facing circumferential stop surface 329 adapted to receive and engage a cap when the module is mounted on a pen as can be seen in FIG. 1B.

The inner ring surface and the outer pen body surface may be in either form-fitting or slight frictional engagement. Each coupling structure on the module is in the form of a latch 322 having a proximal portion 323, a distal portion 324 and a central portion, the latter being pivotally connected to the ring portion by integrally formed flexible hinges 325 allowing the latch to pivot a few degrees corresponding to a circumferential axis. By this arrangement the distal latch portion moves inwards when the proximal portion is moved outwards and vice versa. The proximal latch portions each comprises an inner protrusion 326 adapted to engage a corresponding coupling structure on the pen device and the distal latch portions each comprises a protrusion 327 adapted to engage the cap when a cap is mounted on the pen body by insertion into the circumferential gap 214 (see FIG. 1B) between the logging module and the cartridge holder. To assure correct rotational mounting of the module on the pen the module is provided with a slot (not to be seen) adapted to axially engage a corresponding protrusion on the pen. In the shown embodiment of FIG. 1A the protrusion is provided on the pen cartridge holder 210 and arranged opposite the pen display window 202, the electronic display 130 thereby being arranged next to the pen display window when the module is mounted on a pen. On the body portion 330 the majority of the electronic components 340, a display 341, a cap switch 342 and a battery 343 are mounted. In the shown embodiment the logging module comprises three circumferentially arranged sensors in the form of magnetometers 345 mounted directly on the ring portion 320, the sensors as well as the majority of the electronic components being connected using LDS. The magnetometers and the electronic circuitry are adapted to detect and capture a property value related to the dose amount of drug expelled in the form of rotational movement of a magnetic member of the enclosed expelling mechanism, for example as described in greater detail in PCT/EP2014/056724. Further sensors may be provided allowing e.g. the type of the device to be recognized. For example, a sensor may be provided adapted to detect the colour of the part of the pen on which the logging module is attached or to read a correspondingly arranged barcode.

The logging module may be provided with user input means in the form of e.g. one or more buttons (not shown) allowing the user to control the module, e.g. allowing the user to toggle through log entries. The logging module may further be provided with transmission means allowing data to be transmitted to or from the module, e.g. log data may be transmitted to a user's smartphone by NFC or other wireless means.

Figure 3A:
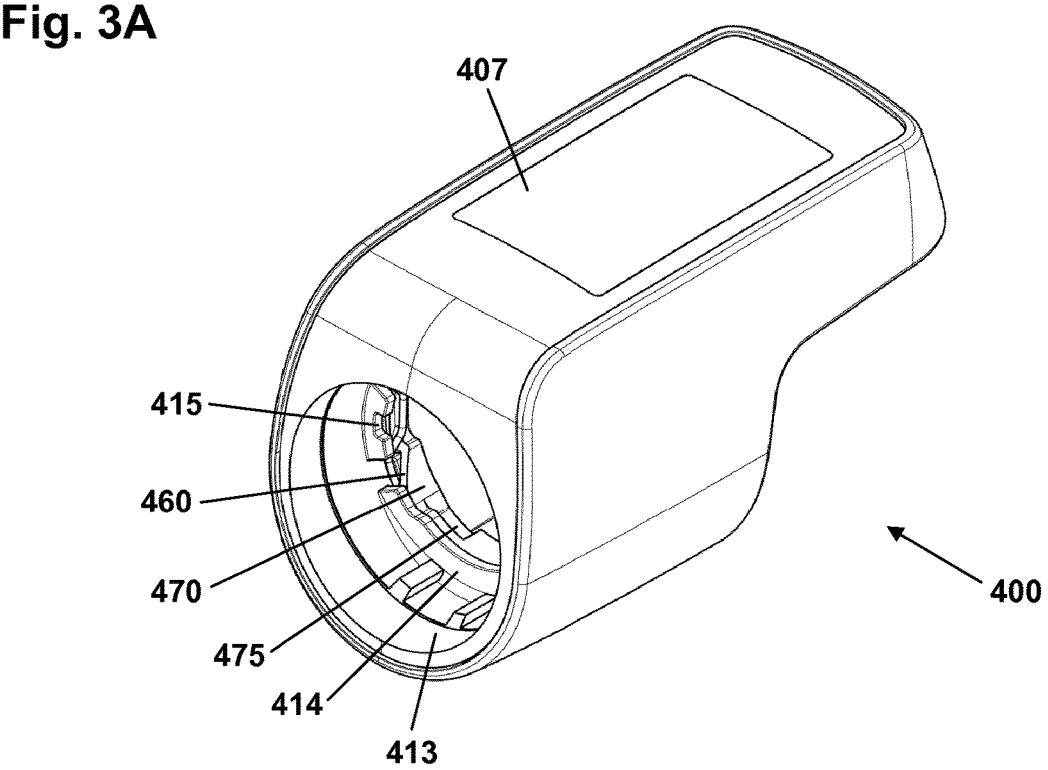
FIG. 3A shows the exterior of a further logging module.
Figure 3B:
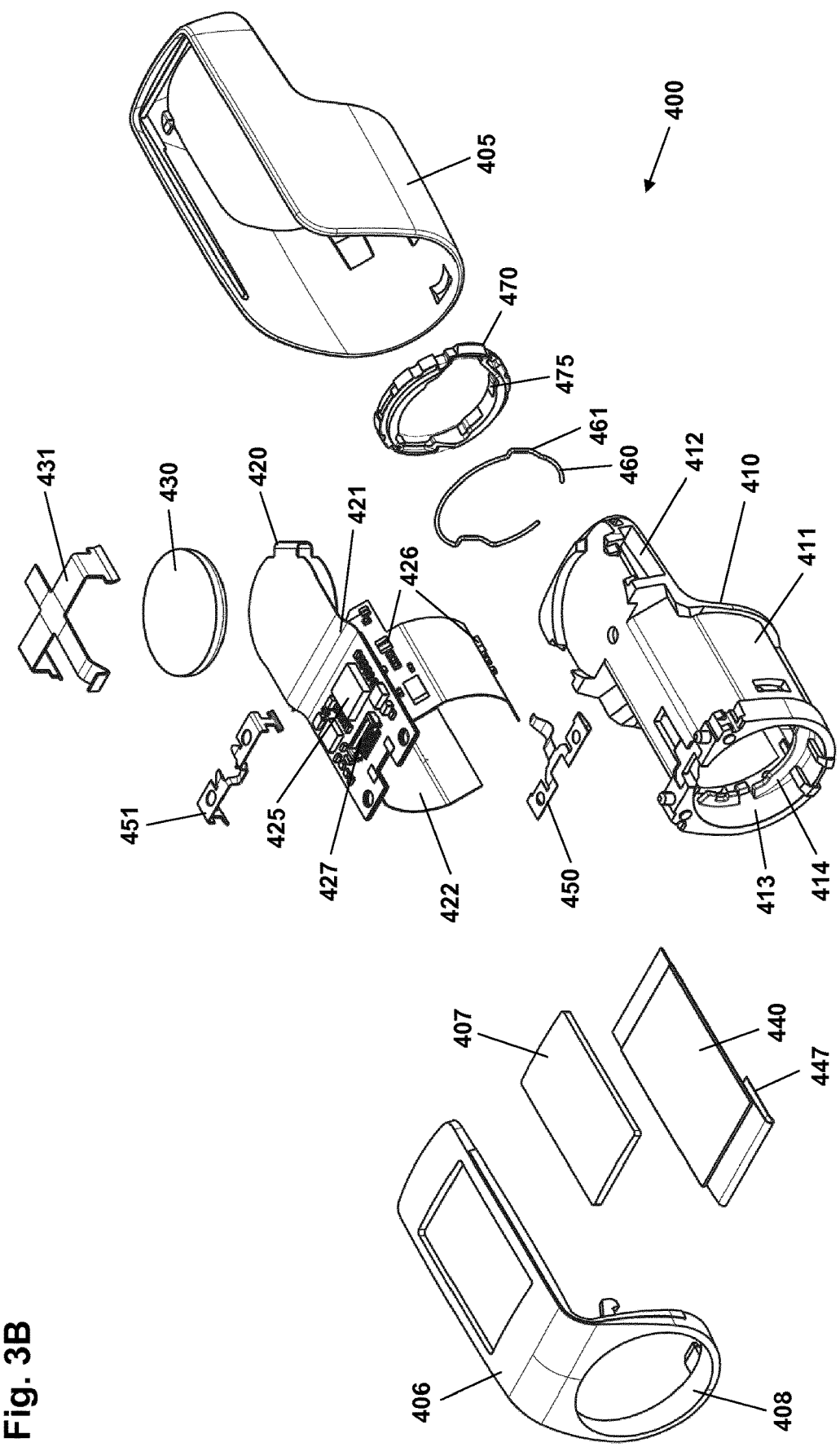
FIG. 3B shows an exploded view of the logging module of FIG. 3A, FIGS. 4A and 4B show the working principle of a snap ring coupling.

Turning to FIGS. 3A and 3B a second exemplary embodiment of a logging module 400 is shown in an assembled respectively an exploded view. The module 400 has the same general appearance as the above described logging module 100 of FIG. 1A and comprises a display window 407 and a bore 413 allowing it to be mounted on a pen device. Instead of being provided with coupling means in the form of latches 322, a flexible snap ring 460 is arranged in the bore and held in place between on the distal side a number of circumferential flange portions 414 formed as part of the housing and on the proximal side an inserted code ring 470 comprising code structures, e.g. cut-outs 475, adapted to engage corresponding code structures formed on the cartridge holder of a corresponding pen device (see below). The flange portions are provided with a pair of opposed cut-outs 415 allowing coupling projections on a pen cartridge holder to engage the snap ring.

Turning to the exploded view of FIG. 3B the module 400 comprises a body member 410 serving as a mounting platform for the different components of the module, the main body providing the "inner" exterior surfaces facing the pen when the module is in its mounted position, the "outer" exterior surface being provided by a cover portion 405 and a display window portion 406, the latter comprising an opening for receiving a transparent window 407 as well as a ring portion 408 forming the cap-facing surface of the module.

The body member 410 has a generally cylindrical ring-formed portion 411 providing a bore 413, and an "upper" portion with an extension 412 on which the majority of the electronic circuitry is mounted. A number of double-sided adhesive tape strips (not shown) are attached to the body member serving to securely hold the flexible printed circuit board (PCB) 420 in place, the PCB comprising a main portion 421 and a pair of opposed "wing" portions 422 adapted to be mounted on the ring-portion. On the PCB a number of electronic components 425, a number of magnetometers 426 as well as a display contact 427 are mounted. The wing portions mainly serve to circumferentially arrange the magnetometers on the ring-portion. A button power cell 430 is connected to the PCB and held in place by a clip 431 adapted to engage the body member. A display 440 is adapted to be mounted on top on the main PCB portion via a flex ribbon cable 447. A body switch member 450 is adapted to be mounted on the body member and cooperate with the PCB, the switch detecting when the logging module has been mounted on a pen body. A cap switch member 451 is adapted to be mounted on the body member and cooperate with the PCB, the switch detecting when the pen cap 207 (see FIG. 1A) is mounted on the pen.

A wire snap member 460 in the form of an open ring is adapted to be mounted in the distally-facing opening of the body member bore. The snap member comprises a pair of opposed coupling sections 461 and serves to reversibly lock the module in place when mounted on a pen body. The wire snap member is described in greater detail below. A code ring 470 is adapted to be mounted in the bore proximally of the snap member. The coding serves to ensure that a given module can be mounted only on the type of pen device to which it is adapted to work, e.g. comprising a given drug in a given concentration. The code ring and the corresponding pen code structure may be coded as described below for the snap ring 670, i.e. comprising a key-and-slot coding. The code ring may also serve to provide a colour coding corresponding to the given coding, this allowing the module to be formed generally in a "generic" colour. The code ring may be used to hold the snap ring in place in the bore. In alternative embodiments the code structures may be arranged on other parts of the logging module and pen.

Figure 4A:
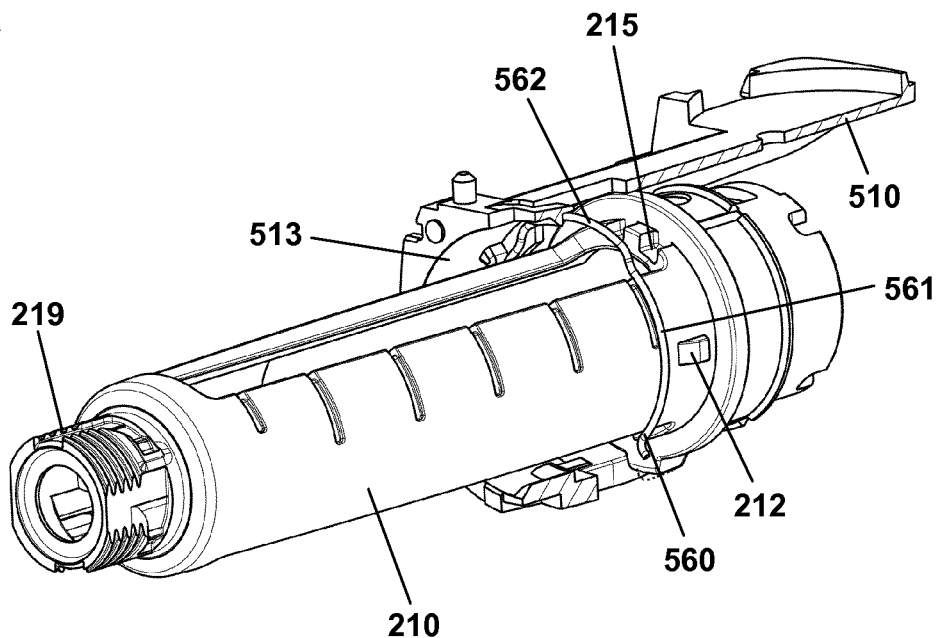
Figure 4B:
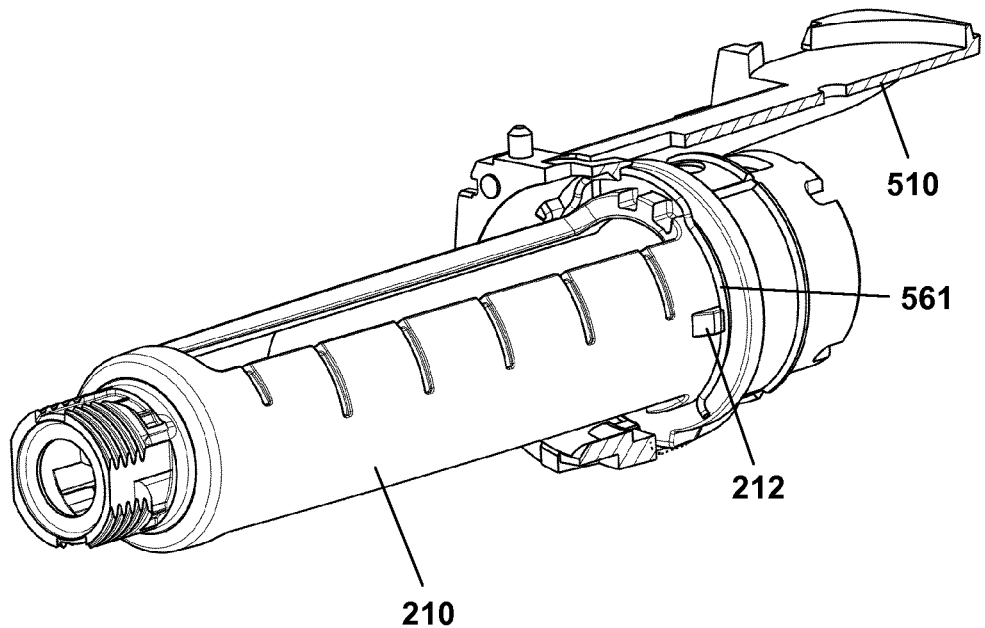

Turning to FIGS. 4A and 4B an alternative embodiment of a module body member 510 with a bore 513 is shown in cross-section, the body member being provided with an open wire snap ring member 560 having a central portion 562 adapted to engage the body member as well as two opposed leg portions 561 each adapted to provide an individual reversible snap lock when engaging corresponding snap coupling means on e.g. a pen cartridge holder. In the shown embodiment the pen snap coupling means is in the form of a pair of opposed protrusions 212 provided proximally on a pen cartridge holder 210, the protrusions also serving to lock a pen cap in place when no logging module is mounted on the pen. In the shown embodiment the cartridge holder proximal portion is provided with a code structure in the form of a pair of cut-outs 215, the code structure being adapted to engage corresponding code projections formed on e.g. a code ring (not shown).

In FIG. 4A the logging module has been partly mounted on a pen (only the cartridge holder is shown), the snap ring abutting the distally-facing sloped surface of the coupling protrusions. When the logging module is moved to its fully mounted position each snap ring leg portion expands laterally and then snaps in place proximally of the coupling protrusion. As the proximally-facing slopes of the coupling protrusions are steeper than the distally-facing slopes the force required to remove the logging device from the pen is greater than when mounting it. The shown snap ring has an open configuration, however, alternatively it may be in the form of a closed ring as long the snap portions of the ring are allowed to move as required by the functionality. As a further alternative the snap ring may be replaced with individual pieces of wire, e.g. for each individual snap coupling, such a wire piece being straight or curved.

Figure 5:
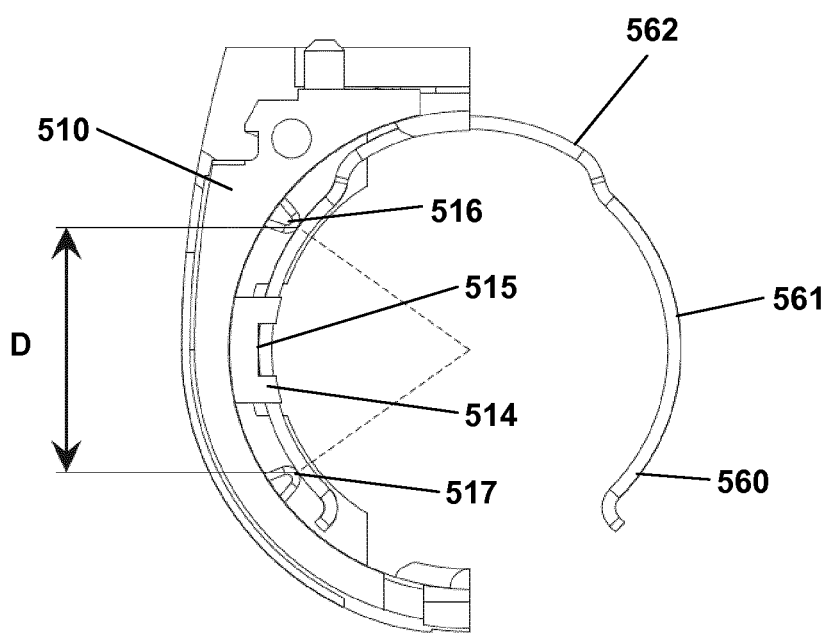
FIG. 5 shows an embodiment of a snap ring coupling.

Turning to FIG. 5 a frontal view of the module body member 510 is shown, the body member being provided with the open wire snap ring member 560 having a central portion 562 adapted to engage the body member as well as a pair of opposed leg portions 561 adapted to provide a reversible snap lock when engaging corresponding snap coupling means on e.g. a pen cartridge holder. The body member comprises a number of circumferential flange portions 514 adapted to hold the ring member in place, cut-outs 515 being provided to allow the above-described coupling projections to slide into engagement with the snap ring member. Corresponding to each snap ring leg portion the body member is provided with a pair of "fulcrum" projections 516, 517 arranged to abut the ring member from the outside, the portion of the ring arranged between the two fulcrum points serving as the actual snap lock portion. In the shown embodiment the fulcrum points are arranged symmetrically relative to the part of the ring adapted to engage the cartridge holder projections 212 (see FIG. 4A). As the projections cause the ring to expand during mounting, bending of the ring will occur around these fulcrum points. By choosing the angle (or equivalent length D) between the fulcrum points, the force required to mount or remove the logging module on the pen cartridge holder can be finely adjusted during the design process. The smaller the distance between the points, the greater the force required.

Figure 6:
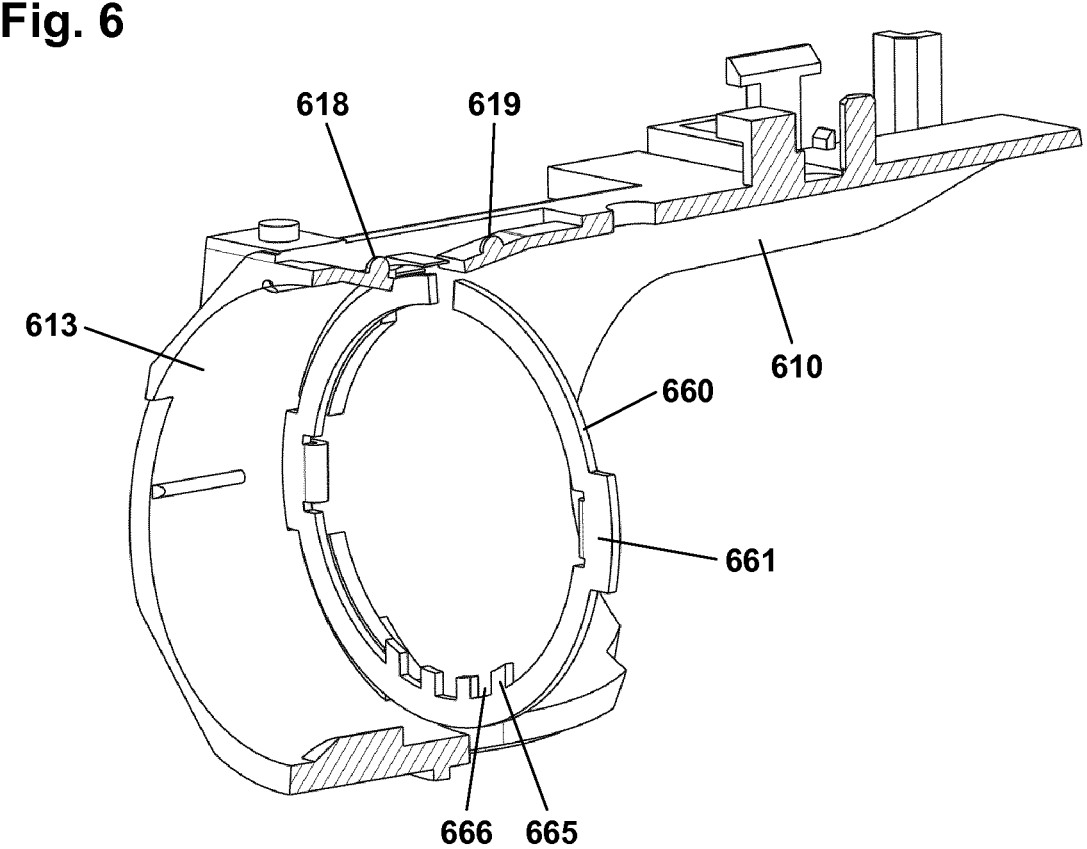
FIG. 6 shows a further snap ring coupling with integrated coding means.
Figure 7A:
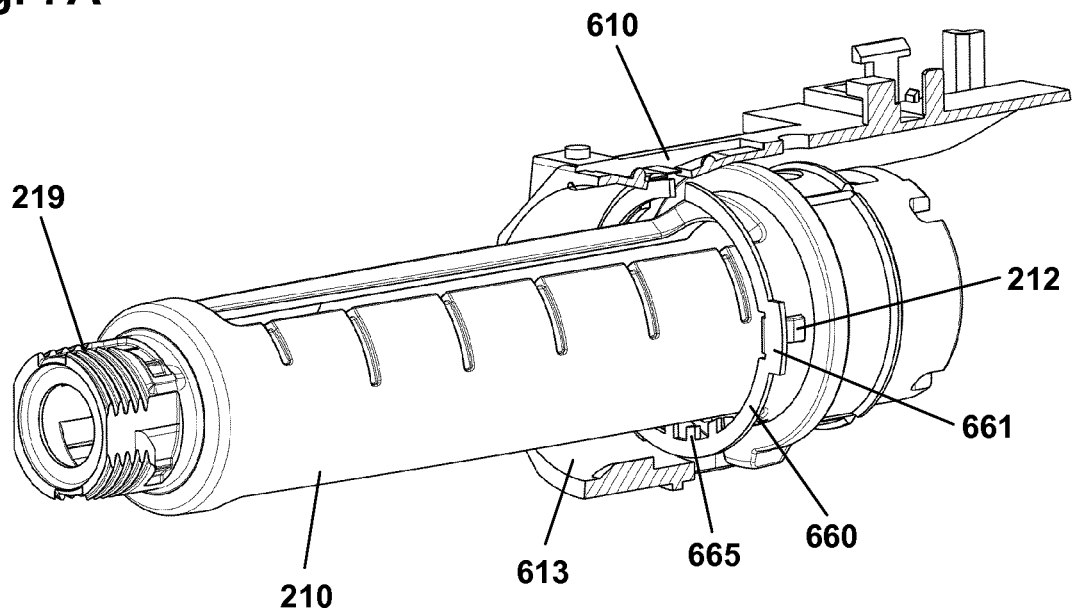
FIGS. 7A and 7B show the working principle of the snap ring coupling of FIG. 6.
Figure 7B:
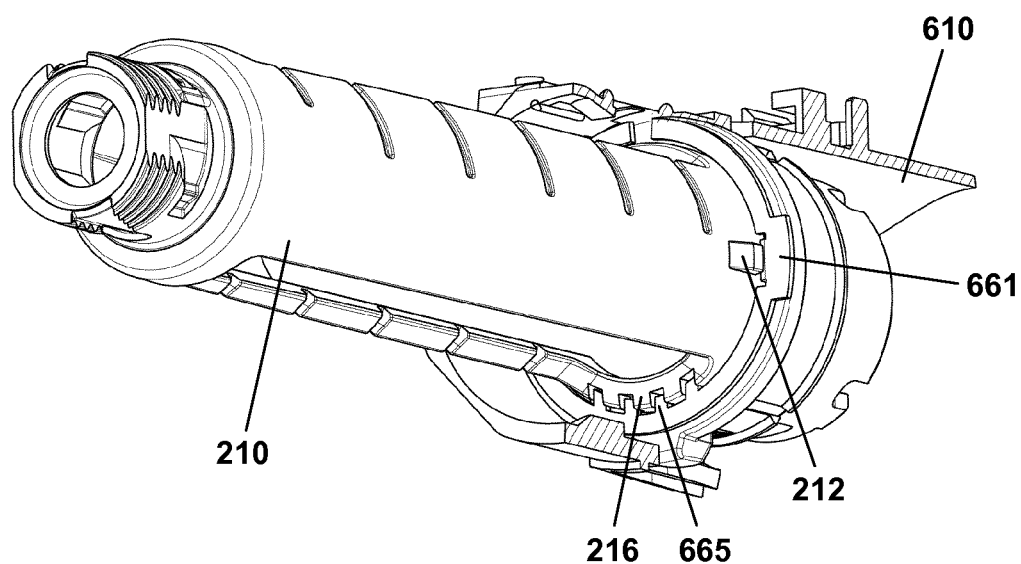

Turning to FIG. 6 a further alternative embodiment of a snap ring arrangement is shown. The module body member 610 shown in cross-section is similar to the body member 510 of FIG. 4A, however, the wire snap ring 560 has been replaced with a plate-based snap ring 660. The ring comprises two dedicated snap portions 661, each comprising a bend-over plate portion providing a rounded surface adapted to slide over a coupling protrusion 212 (see FIG. 7A). In contrast to the wire snap ring 560 the gap in the plate-based ring is smaller and arranged "on top", the "lower" ring part comprising a number of inwardly protruding teeth 665 creating a number of slots 666 there between. The number and positions of slots create a specific coding adapted to receive only a correspondingly coded cartridge holder 210, this corresponding to the coding provided by the code ring 470 in FIG. 3A. As appears, in contrast to the FIG. 4A embodiment the snap ring and coding structure is provided by a single component. When inserting a pen device in the logging module bore 613 as illustrated in FIGS. 7A and 7B the plate-based snap ring 660 works essentially in the same way as the wire snap ring of the FIG. 4A embodiment, the main difference being that the snap ring also provides a coding structure for the pen. In the shown embodiment the cartridge holder 210 is provided with coding protrusions 216 which are received in the coding slots 666, thereby providing a simple mechanical coding of the key-and-slot type. The ring-formed snap member and the bore may be configured such that the ring-formed snap member can be inserted in the bore and snap non-releasable in place.

Not related to the snap ring, the body member 610 comprises a pair of hinged flexible arms 618, 619 serving as actuators for a pair of switches, e.g. dome switches, arranged on a corresponding PCB (not shown). The proximal arm 619 and corresponding switch are actuated when the logging module is mounted on the pen and the distal arm 618 and corresponding switch are actuated when the cap is mounted on the pen.

With reference to FIGS. 1-3 an example of use of the above-described assembly to expel an amount of an insulin formulation will be described. First the user removes the cap from the assembly whereby the logging module is turned on by means of the cap switch 342. The display may show different messages, e.g. the last log entry. For the described embodiment the display is muted after e.g. 5 seconds and will stay muted until the cap is put back in place, this indicating that the user has taken the desired dose. This procedure can also be used if the user wants to check the log entry for the last dose. If not in place a needle assembly is mounted on the cartridge holder coupling 219 after which a flow check can be performed by setting and expelling a small dose of e.g. 2 units (IU) of insulin. The expelled dose is detected by the logging module, however, in the shown embodiment the logging module is adapted to recognise small doses of e.g. 3 IU or less as related to flow check operations for which reason they are not stored as a log entry. After the flow check has been performed the user sets a desired dose of e.g. 50 IU. When the dose is injected this is captured by the logging device and displayed to the user when the cap is re-attached. How the logging unit may be adapted to cope with split or partly delivered doses is described in PCT/EP2014/056727.

The logging module may be configured to store and show data in different ways. To many users the time since last dose and the size of that dose are the most important values. To other users and/or a medical practitioner an overview of the entire log for a given period, e.g.

a week or a month, may be of importance. To allow such an overview the logging module may be provided with output means allowing the dose log to be transferred, e.g. by NFC transfer, to an external display device, e.g. a smartphone or computer for better graphic overview.

The display can be configured to show data in different formats. For example, the display may have two lines in which time is shown using a HH:MM:SS stop watch design, this providing that the time since the last dose expelled from the device can be shown with a running second counter allowing a user to easily identify the shown information as a counting time value. After 24 hours the display may continue to display time in the HH:MM:SS format or change to a day and hour format.

To save energy the display will turn off after a pre-determined amount of time, e.g. 30 seconds. To turn on the display again the user may remove and re-attach the cap.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A logging device adapted to be releasably attached to a drug delivery device, the drug delivery device comprising a drug reservoir or structure for receiving a drug reservoir, drug expelling structure comprising a dose setting structure allowing a user to set a dose amount of drug to be expelled, and a generally cylindrical coupling portion having at least one lateral projection, the logging device comprising:
   electronic circuitry adapted to create a log of expelled dose amounts of drug, comprising:
      sensor structure adapted to capture, when the logging device is attached to the drug delivery device, a property value related to the dose amount of drug expelled from the reservoir by the drug expelling structure during an expelling event,
   a generally cylindrical bore adapted to receive the coupling portion,
   at least one individual snap lock adapted to engage the at least one lateral projection on the drug delivery device, wherein each individual snap lock of the at least one individual snap lock comprises a flexible wire portion arranged circumferentially in the bore and being adapted to be moved laterally by the at least one lateral projection and subsequently snap inwardly when the coupling portion is inserted axially in the bore, and
   a pair of circumferentially arranged support structures serving as fulcrum points for each wire portion when the wire portion is moved laterally by the at least one lateral projection when the coupling portion is inserted axially in the bore,
whereby the logging device and the drug delivery device are axially snap locked to each other.

2. A logging device as in claim 1, wherein the at least one individual snap lock comprises two individual snap locks wherein the two wire portions of the two individual snap locks form a generally ring-shaped wire locking member.

3. A logging device as in claim 2, wherein the generally ring-shaped wire locking member and the bore are configured such that the generally ring-shaped wire locking member can be inserted in the bore and snap non-releasably in place.

4. A logging device as in claim 2, comprising a ring-shaped member mounted in the cylindrical bore and adapted to hold the generally ring-shaped wire locking member non-releasably in place.

5. A logging device as in claim 1, wherein at least a portion of each flexible wire portion is formed from metal.

6. A logging device as in claim 1, wherein the sensor structure is adapted to capture a property value in the form of an amount of rotation of a magnetic member arranged in the drug delivery device, the amount of rotation of the magnetic member corresponding to the dose amount of drug expelled from the reservoir by the drug expelling structure.

7. An assembly comprising a logging device as in claim 1, in combination with a drug delivery device comprising a drug reservoir or structure for receiving a drug reservoir, drug expelling structure comprising a dose setting structure allowing a user to set a dose amount of drug to be expelled, and a generally cylindrical coupling portion having at least one lateral projection,
   wherein the logging device is releasably attachable to the drug delivery device.

8. A medical system comprising a first logging device as in claim 2, in combination with first and second drug delivery devices each comprising a drug reservoir or structure for receiving a drug reservoir, drug expelling structure comprising a dose setting structure allowing a user to set a dose amount of drug to be expelled, and a generally cylindrical coupling portion having at least one lateral projection, wherein:
   each generally cylindrical coupling portion comprises a coding structure,
   the first logging device comprises a coding structure associated with the generally cylindrical bore,
   the coding structures on the first and second drug delivery devices and on the first logging device are configured to:
      (i) allow the first drug delivery device to be received and releasably locked in the bore of the first logging device,
      (ii) prevent the second drug delivery device to be received and locked in the bore of the first logging device, and
   the drug delivery devices in the system are based on the same technology platform by having at least 50% interchangeable parts.

9. A medical system as in claim 8 further comprising a second logging device, wherein:
   the second logging device comprises a coding structure associated with a generally cylindrical bore, the coding structures on the first and second drug delivery devices and on the second logging device are configured to:

allow the second drug delivery device to be received and releasably locked in the bore of the second logging device, and prevent the first drug delivery device to be received and locked in the bore of the second logging device.

10. A medical system as in claim 9, wherein each of the first and second logging devices comprise a ring-shaped code member comprising the coding structure and being mounted in the generally cylindrical bore.

11. A medical system as in claim 10, wherein the second logging device further comprises a generally ring-shaped wire locking member, and wherein each ring-shaped code member of the first and second logging devices is adapted to hold the respective generally ring-shaped wire locking member non-releasably in place.

12. A medical system as in claim 8, wherein the coding structures of the drug delivery devices correspond with the coding structure of the first logging device in a key-and-slot manner.

* * * * *

UNITED STATES PATENT AND TRADEMARK OFFICE
CERTIFICATE OF CORRECTION

| | | |
|---|---|---|
| PATENT NO. | : 10,603,442 B2 | Page 1 of 1 |
| APPLICATION NO. | : 15/505423 | |
| DATED | : March 31, 2020 | |
| INVENTOR(S) | : Jakobsen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 261 days.

Signed and Sealed this
Sixth Day of October, 2020

Andrei Iancu
*Director of the United States Patent and Trademark Office*